United States Patent [19]

Spellitz

[11] Patent Number: 5,243,367
[45] Date of Patent: Sep. 7, 1993

[54] OPTICAL SYSTEM FOR MEASURING THE HUMAN CORNEA

[76] Inventor: Fritz Spellitz, Schönbrunner Strasse 217, A-1120 Vienna, Austria

[21] Appl. No.: 734,522

[22] Filed: Jul. 23, 1991

[30] Foreign Application Priority Data

Jul. 24, 1990 [AT] Austria .................................. 1555/90

[51] Int. Cl.⁵ ................................................ A61B 3/10
[52] U.S. Cl. .................................... 351/212; 351/221; 351/247
[58] Field of Search ............... 351/205, 211, 212, 221, 351/247

[56] References Cited

U.S. PATENT DOCUMENTS

| 4,093,340 | 6/1978 | Klose . |
| 4,838,679 | 6/1989 | Bille ..................................... 351/221 |
| 4,925,301 | 5/1990 | Rafanelli . |

FOREIGN PATENT DOCUMENTS

| 8602249 | 4/1986 | European Pat. Off. . |
| 0210722 | 2/1987 | European Pat. Off. . |
| 034601 | 12/1989 | European Pat. Off. . |
| 2524152 | 5/1975 | Fed. Rep. of Germany . |

Primary Examiner—Rodney B. Bovernick
Attorney, Agent, or Firm—Anderson Kill Olick & Oshinsky

[57] ABSTRACT

An optical system for measuring the human cornea includes a light source, a scanner, an optical deflecting system, a sensor and an evaluating unit. A rotating mirror is used as the scanner and a plurality of stationary plane deflecting mirrors are arranged in the path of the rotating light beam. With increasing distance of the deflecting mirrors from the eye, the deflecting mirrors direct the light beam onto points of the cornea surface which are located increasingly closely to the frontmost point of the cornea.

4 Claims, 3 Drawing Sheets

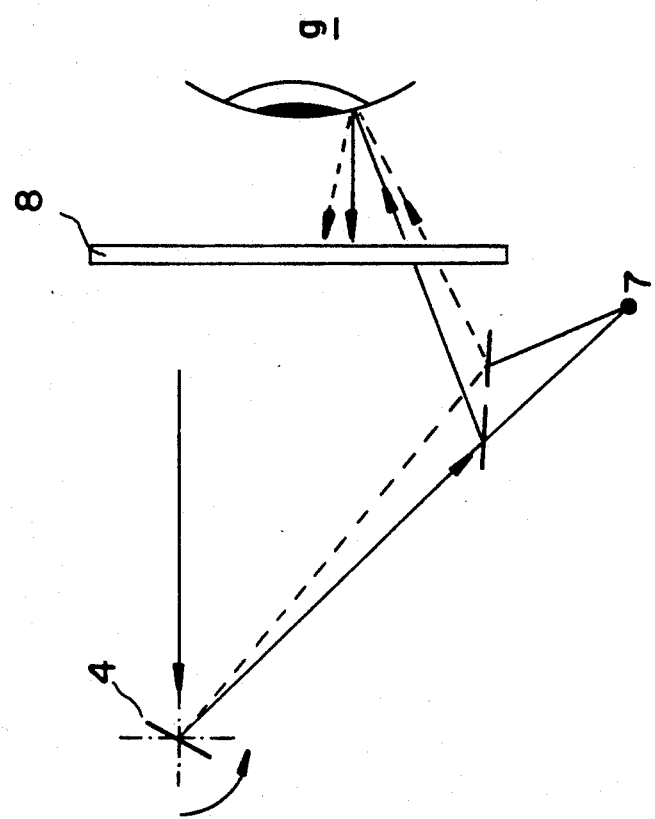

OPTICAL SYSTEM FOR MEASURING THE HUMAN CORNEA

BACKGROUND OF THE INVENTION

1. Field of the Invention

The present invention relates to an optical system for measuring the human cornea. The system includes a light source, a scanner, an optical deflecting system, a sensor and an evaluating unit. The system is used by placing the eye in front of the optical deflection system.

2. Description of the Related Art

A measuring system of the above-described type is known particularly from DE-T1-35 90 539. This document was first published in the English language as WO/86/02249. The reference discloses an arrangement of a laser measuring system including scanner, sensor and evaluating unit. A holographic element is used as a focusing device closely in front of the eye. This holographic element is selected in such a way that, in the case of an ideal positioning of an ideal cornea, the beam reflected by the cornea surface coincides with the incoming beam. Accordingly, for evaluating the data, it is necessary to place in the path of the beam a beam divider which deflects a portion of the reflected beam onto an area sensor. This beam divider simultaneously deflects a portion of the beam directed by the laser through a scanner onto a second two-dimensional sensor whose output signals inform a computer as to how the emitted light beam is directed at a given moment. From the data and from the knowledge of the stationary geometry or the geometry at a given moment, the computer is capable of computing the shape of the cornea surface.

However, this known arrangement has several significant disadvantages.

The holographic element must be of a large size in order to always effect the theoretically correct angle of incidence on the eye. Only when this requirement is met, is it possible to obtain the measurement result in the range of the area sensor and to obtain a measured value in this manner.

The area sensors themselves limit the measurement accuracy and dissolution and are expensive. In order to obtain the desired measurement accuracy, it is necessary to select appropriately large spacings. However, it is not only necessary to consider the beam expansion on the positively curved cornea, but it must also be taken into consideration that, in the case of injury to the surface of the cornea, significant deviations of the surface normal from the ideal condition can occur, so that it is possible that several measurement points successively do not provide a measurement value because the reflected beam can no longer reach the area sensor.

The beam divider represents another significant disadvantage. While the beam divider advantageously offers the possibility of providing the computer with information concerning the position of the beam at a given moment, the beam divider simultaneously weakens the beam reflected by the eye, so that it is necessary to radiate the eye with an intensity which is sufficient for ensuring that the reflected beam after the partial reflection at the beam divider is still reliably capable of appropriately activating the area sensor. However, this increased light intensity is an extremely unpleasant additional burden to the eye.

Additional problems are due to the fact that the length of the path of the beam from the scanner to the reference area sensor is significantly shorter than the length of the path of the reflected beam. The angle of incidence and, thus, the angle of the emitted beam from the beam divider is the same as the corresponding angle of the reflected beam, however, the emitted beams and, thus, also the image thereof on the reference area sensor, diverge over the entire measurement range, as seen projected over the beam divider. This does improve the measurement accuracy, however, again represents a limitation in the possibilities of arranging the scanner, the beam divider and the reference area sensor.

DE-OS 25 24 152 discloses another optical system, although intended for measuring large plane surfaces. In this system, a rotating light beam is reflected by stationary deflecting mirrors in such a way that the light beam covers during its rotation the entire area to be scanned. However, the reference does not disclose the manner of the actual determination of the measurement values, i.e., nothing is disclosed concerning reflected beam, type of scanner, etc.

SUMMARY OF THE INVENTION

Therefore, it is the object of the present invention to provide a measuring system which avoids the disadvantages described above. In particular, the intensity of the laser beam directed onto the eye is to be kept as low as possible. The system should not require an expensive and sensitive holographic element. Moreover, the invention should make it possible to use, instead of area sensors, linear sensors which are more responsive and more accurate and still less expensive.

In accordance with the present invention, the above object is met by using a rotating mirror as a scanner in the known manner. The optical deflecting system is formed by a plurality of stationary plane deflecting mirrors, wherein the surfaces of the individual mirrors are arranged tangentially relative to a curved line which is located in the plane generated by the rotating light beam of the rotating mirror. With increasing distance of a deflecting mirror from the cornea, the light beam is directed to points of the cornea surface which are located increasingly closely to the frontmost point of the cornea.

As a result of the features of the present invention, the laser beam reflected by the eye is directed immediately onto the sensor. The invention further provides the surprising effect that the beams deflected by the deflecting mirrors onto the eye each reach the corresponding portion of the cornea surface at such an angle that the best possible evaluation on the sensor is possible without the positioning of the sensor requiring contradictory conditions.

The sensor is preferably a linear sensor. This inexpensive and space-saving feature is possible because the beam deflection takes place only in one plane.

In accordance with an advantageous feature of the present invention, the surfaces of the deflecting mirrors are arranged obliquely relative to the plane of the rotating light beam and the deflecting mirrors direct the light beams exactly onto points which correspond to a certain radius or diameter of an ideal cornea surface. As a result, during the scanning procedure always one cornea radius or diameter is measured when the measurement arrangement is turned about the eye axis, so that the cornea surface can be measured radius by radius or diameter by diameter. Because of the oblique arrangement, the measured points of the cornea are located exactly on a radius or diameter of the ideal cornea surface.

Of course, it is also possible to use a different system and to displace the measurement arrangement by a certain extent vertically or horizontally in order to reach measuring points which at least essentially determine a Cartesian system of coordinates.

In order to obtain the best possible correlation between the light beam emitted at any given moment and the measured reflected light beam, another feature of the invention provides that at least two of the deflecting mirrors deflect the incoming beam onto a monitoring element for the beam passage. As a result, since the geometric configuration is known and since it can practically always be assumed that no significant variations in the angular speed of the rotating mirror occur as the mirrors are being covered, it is possible to effect for each measuring point an excellent correlation of the incoming beam with the reflected beam. The accuracy is further increased by using more than two mirrors.

In accordance with another advantageous further development of the invention, always two, preferably adjacent, deflecting mirrors are directed to one and the same point of the ideal cornea surface, so that the redundancy of the measuring value is increased and the effects of movements of the eye, etc. can be eliminated almost completely.

The arrangement according to the present invention also makes it possible to avoid the long beam path necessary in the known devices, particularly of the reflected light beam. As a result, the beam expansion which inevitably occurs at the positively curved cornea surface can be kept small, so that it is possible to use more finely divided sensors or analog sensors because a more focused signal is received.

The terminology "measuring point" is to be evaluated while taking into consideration the prevailing conditions. The rotating scanner mirror and the successive passage of the deflecting mirrors create oblong areas on the eye whose reflections generally locally overlap on the sensor. The computer either is supplied with an appropriately averaged measuring value or such a measuring value is determined by the computer.

The various features of novelty which characterize the invention are pointed out with particularity in the claims annexed to and forming a part of this disclosure. For a better understanding of the invention, its operating advantages attained by its use, reference should be had to the drawing and descriptive matter in which there are illustrated and described preferred embodiments of the invention.

BRIEF DESCRIPTION OF THE DRAWINGS

In the drawing:

FIG. 3 is schematic illustration of another embodiment of the measuring system according to the present invention.

DESCRIPTION OF THE PREFERRED EMBODIMENTS

Figure 1:
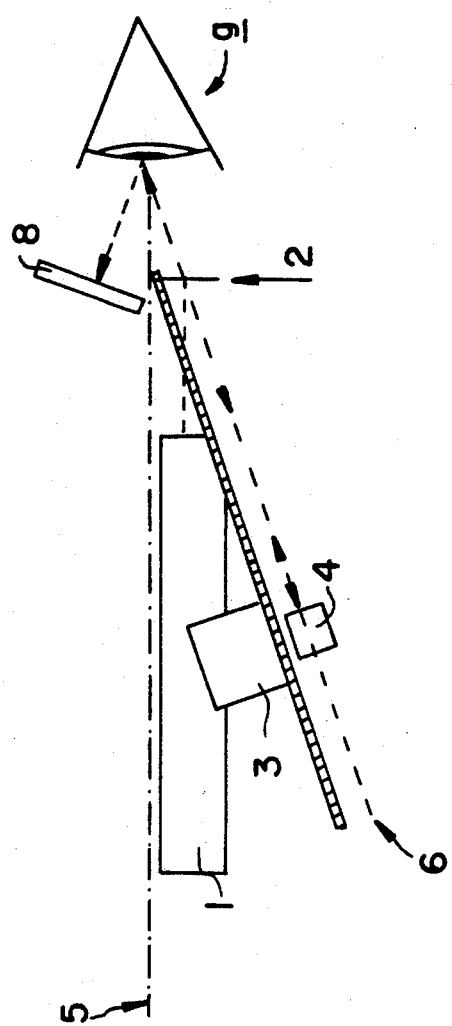
FIG. 1 is a schematic side view of a first embodiment of a measuring system according to the present invention.

The measuring system illustrated in the drawing rotates about the optical axis of the eye to be measured. The illustration of FIG. 1 of the drawing corresponds to the position in which the horizontal cornea diameter is to be measured.

Figure 2:
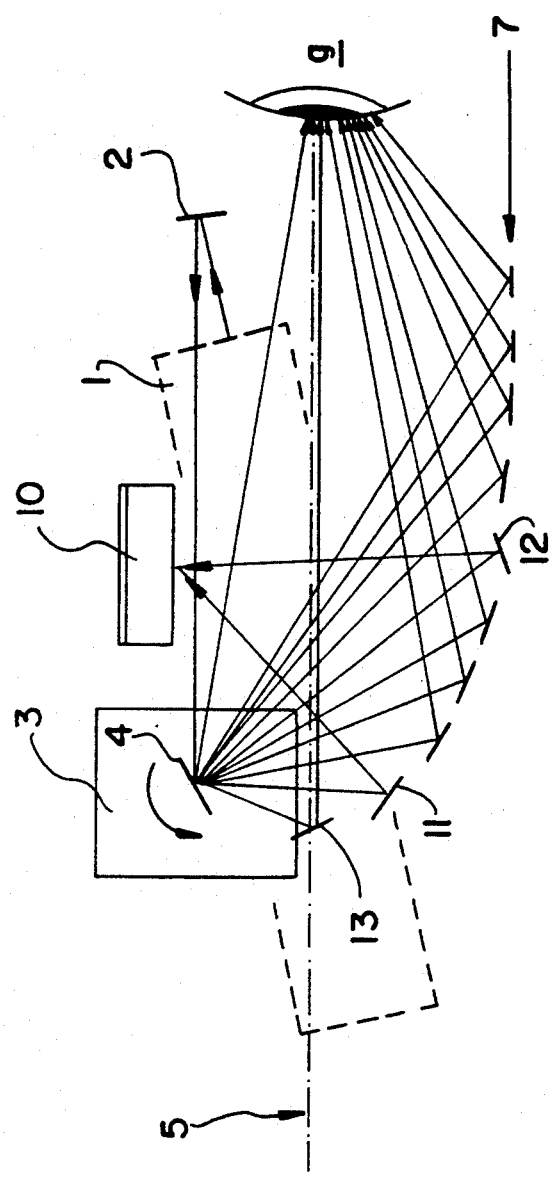
FIG. 2 is a top view of the measuring system of FIG. 1.

FIG. 2 of the drawing shows in a top view the pattern of the beams reaching the cornea surface via the deflecting mirrors.

A laser 1 emits a light beam which reaches via a deflecting mirror 2 a rotating mirror 4 of the scanner 3. The laser beam which is spread out by the scanner mirror 4 is situated in the plane of the drawing of FIG. 2. In the following, this plane shall be called the image plane. The optical axis of the laser 1 includes an angle of preferably about 20° with the image plane 6. As a result, it is possible to arrange the laser 1, the scanner 3 including scanner mirror 4, the deflecting mirrors 7 and the sensor 8 in an advantageous manner in different planes. The light beam emitted by the laser 1 extends from the deflecting mirror 2 in the image plane 6, so that the mirror 2 does not extend perpendicularly relative to this plane.

If, as mentioned above, the deflecting mirrors 7 do not extend perpendicularly to the image plane 6, the emitted beams between the mirrors and the eye also do not extend in the image plane. Thus, it is possible to compensate for the fact that the section of the image plane with the eye is not an exact radius or diameter. This slight oblique position is not taken into consideration in the drawings.

As shown in FIG. 2, two of the deflecting mirrors are not directed toward the eye 9 but rather toward a control sensor 10. The two control mirrors 11, 12 deflect the passing laser beam onto the control sensor 10 which accurately determines the beam passage with respect to time and, thus, facilitates an accurate correlation of the beam reaching the eye 9 with the beam reflected by the eye 9 to the sensor 8. Of course, it is possible to provide a third control mirror or to adjust others of the deflecting mirrors 7 as control mirrors. The mirrors 11, 12 can assume an oblique position independently of the mirror 7.

It is further possible to place the scanner mirror 4 more closely to the axis of rotation 5 and to provide a second row of deflecting mirrors symmetrically to the deflecting mirror 7, in order to scan a larger number of measuring points for each rotation of the scanner mirror 4. In the arrangement just described, as well as in the arrangement illustrated in the drawing, it is also possible to direct always two or more of the deflecting mirrors onto the same point on the surface of the cornea, in order to increase the redundancy and, thus, to improve the measuring accuracy and measuring security.

It is further possible to direct the deflecting mirrors 7 in such a way that the emitted beam intersects the axis 5 shown in FIG. 2 and to reach the upper half of the eye, as seen in FIG. 2. This may make it possible to further improve the angle of incidence of the beam.

It is of course also possible to provide a combination of the above-described features.

The evaluation of the measurement results takes place in the conventional manner by means of an evaluating unit 8A including a computer which, from the geometric configuration of the measurement arrangement, the rate of rotation of the mirror 4 and the measurement results on the control sensor 10 and the sensor 8 with respect to time and space, determines the position in space of the respective measuring point on the eye 9. Moreover, the computer is, of course, capable of carrying out all other computations which are necessary for forming a cornea model, for example, the computer is capable of determining the tangential plane in individual points or the curvature of the cornea in accordance with predetermined planes.

As is evident from FIG. 2, the measurement arrangement according to the present invention makes it also possible to direct the beam received from the scanner mirror 4 onto the eye directly and without previous reflection on a deflecting mirror 7. This possibility is of particular significance when the scanner mirror 4 is located particularly closely to the axis of rotation 5 or when the scanner mirror 4 has a great distance from this axis, because it is then possible to obtain a favorable reflection on the eye for the sensor 8.

The deflecting mirror 13 located exactly on the axis 5 as shown in FIG. 2 can be utilized for determining the position of the frontmost point of the eye.

Different types of construction can be used for the sensor 8. It is also possible to arrange two or more linear sensors 8 immediately adjacent and parallel to each other, but with measuring sections which are appropriately offset in axial direction, in order to be able to exactly determine the position of the beam which is reflected by the eye 9. Of course, it is also possible that the computer carries out an interpolation or correlation of the signals received from the individual linear sensors.

Since the control sensor 10 receives the beam reflected by the control mirrors 11, 12 in an exactly predeterminable plane, the control sensor 10 does not require the arrangements described with respect to sensor 8. The important consideration is that the sensor 10 is selected with respect to accuracy and measuring speed in such a way that it is capable of exactly determining the point in time when the beam passes through.

As can be seen in FIGS. 1 and 3, the sensor 8 is located closely near the eye 9, so that the beam to be measured is not yet expanded by the double-positively curved cornea surface in such a way that it could influence the measuring axis.

The arrangement according to the present invention may be realized in many different ways which deviate from the illustrated embodiment. Thus, it is possible to adjust a different angle between the laser axis and the image plane. The deflecting mirrors 7 as well as the other mirrors are commercially available conventional mirrors which are suitable for reflecting laser light. It is even possible to use instead of the laser a light source which emits a sharply focused beam whose composition of wave length is such that no undue expansion occurs as a result of the reflection on the eye 9. However, the use of a laser is preferred.

It is also possible to omit the deflecting mirror 2, however, in that case the laser and its laser beam axis must be located in the image plane 6 which makes a compact arrangement difficult. On the other hand, it is possible to provide several deflecting mirrors, so that the laser arrangement is more flexible.

The measuring arrangement is rotated about the axis 5 preferably by means of a stepping motor which acts on the measuring arrangement either with or without an intermediately arranged transmission. Of course, the angular position of the measuring system relative to the axis of rotation 5 is also supplied to the computer.

The above-described measuring system is not only suitable for measuring the cornea surface. Rather, the system is suitable for all small surfaces or bodies which have reflecting surfaces, particularly curved surfaces.

While specific embodiments of the invention have been shown and described in detail to illustrate the inventive principles, it will be understood that the invention may be embodied otherwise without departing from such principles.

I claim:

1. An optical system for measuring a human cornea having a cornea surface, comprising:
   a light source;
   a scanner formed as a rotating mirror;
   an optical system for deflecting a scanning light beam, emitted by said rotating mirror, toward the cornea surface positionable in front of said optical deflecting system;
   a sensor for receiving a light beam reflected by the cornea surface; and
   an evaluating unit for receiving a signal generated by said sensor in response to receiving the reflected light beam;
   wherein said optical deflecting system includes a plurality of stationary plane deflecting mirrors having surfaces which are arranged tangentially relative to a curved line which is located in a plane generated by the rotating light beam emitted by said rotating mirror, said deflecting mirrors being arranged at increased distances from the cornea surface, so that the rotating light beam which is deflected by a deflecting mirror located farther away from the cornea surface is directed to a point of the cornea surface which is correspondingly closer to a frontmost point of the cornea surface.

2. The optical system of claim 1, wherein said sensor is a linear sensor.

3. The optical system of claim 1, wherein said surfaces of said deflecting mirrors are arranged at an oblique angle relative to a plane of said rotating light beam, and wherein said deflecting mirrors are positioned so as to direct said light beam exactly onto points which correspond to one of a predetermined radius and diameter of the cornea surface.

4. The optical system of claim 1, wherein at least two adjacent deflecting mirrors direct respective light beams onto a same point of the cornea surface.

* * * * *